(12) United States Patent
Gabriele et al.

(10) Patent No.: US 11,939,444 B2
(45) Date of Patent: Mar. 26, 2024

(54) MODIFIED POLYMER FILM SURFACES FOR SINGLE-USE BIOREACTOR BAGS AND BIOCONTAINMENT AND METHODS OF FORMING SAME

(71) Applicant: THE SECANT GROUP, LLC, Telford, PA (US)

(72) Inventors: Peter D. Gabriele, Frisco, TX (US); Jeremy J. Harris, Doylestown, PA (US); Scott Radzinski, Gilbertsville, PA (US); Brian Ginn, Harleysville, PA (US); Ryan R. Smalley, Lansdale, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 199 days.

(21) Appl. No.: 17/226,718

(22) Filed: Apr. 9, 2021

(65) Prior Publication Data

US 2021/0317278 A1    Oct. 14, 2021

Related U.S. Application Data

(60) Provisional application No. 63/007,523, filed on Apr. 9, 2020.

(51) Int. Cl.
*C08J 7/12* (2006.01)
*B05D 3/10* (2006.01)
(Continued)

(52) U.S. Cl.
CPC ............... *C08J 7/12* (2013.01); *B05D 3/101* (2013.01); *B05D 7/04* (2013.01); *C08J 7/0427* (2020.01);
(Continued)

(58) Field of Classification Search
CPC ...... B05D 3/101; B05D 7/04; B05D 2201/02; B05D 2350/30; B05D 2508/00; C08J 7/0427; C12M 23/14; C12M 23/28
See application file for complete search history.

(56) References Cited

U.S. PATENT DOCUMENTS 8,143,042 B2 * 3/2012 Bettinger ........... C08G 63/6854
435/395
10,500,031 B2  12/2019 Levinson
(Continued)

FOREIGN PATENT DOCUMENTS

EP      619178 A1 * 10/1994 ............. B32B 27/08
EP     0619178 A1   10/1994
JP    2019131770 A *  8/2019

OTHER PUBLICATIONS

Gaston et al., "FTIR study of ageing of γ-irradiated biopharmaceutical EVA based film", Polymer Degradation and Stability, vol. 129, pp. 19-25 (2016).

*Primary Examiner* — James C Goloboy
(74) *Attorney, Agent, or Firm* — McNees Wallace & Nurick LLC

(57) ABSTRACT

In some embodiments, a polymer film includes a base composition of poly(ethylene-vinyl acetate) and a surface composition comprising hydroxy groups. In some embodiments, a polymer film includes a base layer of a first composition of poly(ethylene-vinyl acetate), a surface layer at a surface of the base layer, and a coating layer of a second composition of a copolymer of glycerol and sebacic acid. The surface layer includes surface hydroxy groups converted from acetate groups of the poly(ethylene-vinyl acetate). The second composition is attached to the surface layer by ester bonds between carboxyl groups of the copolymer and the hydroxy groups. A single-use bioreactor bag includes a polymer film including a base composition of
(Continued)

poly(ethylene-vinyl acetate) and a surface composition comprising hydroxy groups. A method of modifying a poly(ethylene-vinyl acetate) film includes converting acetate groups at a first surface of the poly(ethylene-vinyl acetate) film to hydroxy groups.

19 Claims, 8 Drawing Sheets

(51) Int. Cl.
*B05D 7/04* (2006.01)
*C08J 7/04* (2020.01)
*C12M 1/00* (2006.01)

(52) U.S. Cl.
CPC ............ *C12M 23/14* (2013.01); *C12M 23/28* (2013.01); *B05D 2201/02* (2013.01); *B05D 2350/30* (2013.01); *B05D 2508/00* (2013.01); *C08J 2331/04* (2013.01); *C08J 2467/00* (2013.01)

(56) References Cited

U.S. PATENT DOCUMENTS

| | | | | |
|---|---|---|---|---|
| 2003/0194668 | A1* | 10/2003 | Kawanishi | C08B 3/24 |
| | | | | 430/641 |
| 2016/0251540 | A1* | 9/2016 | Nicholson | C08G 81/00 |
| | | | | 504/360 |
| 2019/0218507 | A1* | 7/2019 | Gabriele | C12M 23/26 |
| 2020/0010799 | A1* | 1/2020 | Ma | C12N 5/0068 |

* cited by examiner

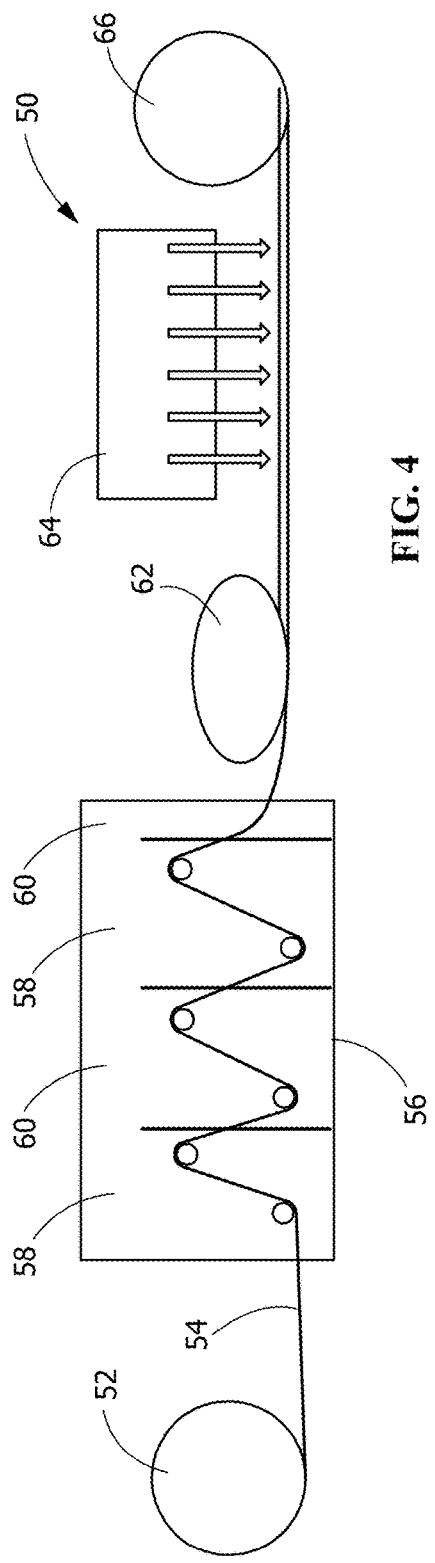
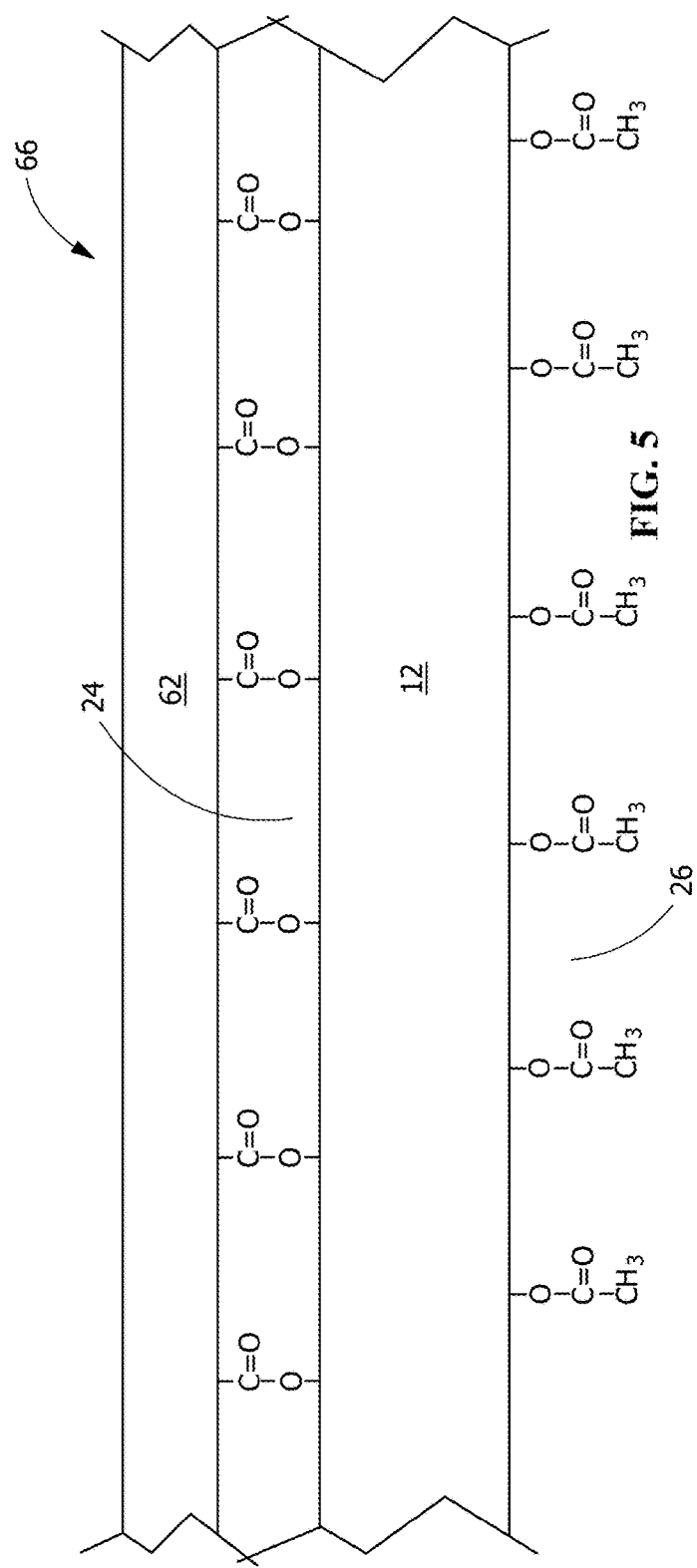
FIG. 4
FIG. 5

MODIFIED POLYMER FILM SURFACES FOR SINGLE-USE BIOREACTOR BAGS AND BIOCONTAINMENT AND METHODS OF FORMING SAME

CROSS-REFERENCE TO RELATED APPLICATIONS

This application claims priority to and the benefit of U.S. Provisional Application No. 63/007,523 filed Apr. 9, 2020, which is hereby incorporated by reference in its entirety.

FIELD OF THE INVENTION

The present disclosure is generally directed to single-use bioreactor bags for cell-based manufacturing and therapeutic use. More specifically, the present disclosure is directed to poly(ethylene-vinyl acetate) (PEVA) films with a surface modification to poly(ethylene-vinyl alcohol) (PEVOH), as well as polyvinyl acetate (PVA) with a surface modification to polyvinyl alcohol (PVOH), that may be appropriate for single-use bioreactor (SUB) bags and biocontainment constructs.

BACKGROUND OF THE INVENTION

A single-use bioreactor bag promotes cell growth or cell production of a particular target biologic in a contained cell culture medium in the bag. The bag is typically made of a polymer film, which is disposed of after collection of the cultured cells or produced biologics. Single-use bioreactor bags are significantly less expensive than conventional bioreactor systems and obviate cleaning and sterilization after use.

Certain preferred polymer materials for single-use bioreactor bags include the presence of phthalates during formation, which can still be present in low amounts in the resulting single-use bioreactor bag and negatively affect the bioreactor.

Although generally not needed for many types of bioreactor bags, such as, for example, those used for cell proliferation, an oxygen barrier or other gas barrier, which is not provided by many conventional polymer materials used in single-use bioreactor bags, may be needed for certain bioreactors. For example, PEVA films or layers tend to be gas permeable barrier layers. In cases requiring a gas barrier layer, a multilayer film employing PEVOH as a barrier layer may be used.

The SUB industry has borrowed the multilayer concept from the food industry without reasonable thought as to why a food-grade film benefits the SUB design. Separate PEVOH films or coatings are often sandwiched between two appose acetate films to create a multilayer construction with a gas barrier. This construct also requires "tie layer" chemistries between the acetate and polyol chemical surfaces to enhance multilayer compatibility. Commercial multilayer films for SUB bags may have a film thickness of 15 mil (380 μm) or greater. Additionally, off-the-shelf films available from the food industry cannot be readily modified.

BRIEF DESCRIPTION OF THE INVENTION

There is a need for a thin, customizable universal polymer film for single-use bioreactor bags having gas barrier capabilities and being free of trace amounts of certain undesirable extractables and leachables from polymer formation.

In exemplary embodiments, a polymer film includes a base composition of poly(ethylene-vinyl acetate) and a surface composition including hydroxy groups.

In exemplary embodiments, a polymer film includes a base layer of a first composition of poly(ethylene-vinyl acetate), a surface layer at a surface of the base layer, and a coating layer of a second composition of a copolymer of glycerol and sebacic acid. The surface layer includes surface hydroxy groups converted from acetate groups of the poly (ethylene-vinyl acetate). The second composition is attached to the surface layer by ester bonds between carboxyl groups of the copolymer of glycerol and sebacic acid and the hydroxy groups.

In exemplary embodiments, a single-use bioreactor bag includes a polymer film including a base composition of poly(ethylene-vinyl acetate) and a surface composition including hydroxy groups.

In exemplary embodiments, a method of modifying a polymer film includes converting acetate groups at a first surface of a poly(ethylene-vinyl acetate) film to hydroxy groups.

In exemplary embodiments, a process converts an acetate functional chemistry of a portion of a PEVA film to an alcohol functional chemistry through saponification, radiation oxidation, plasma treatment, laser ablation/oxidation, or other like methods.

In exemplary embodiments, an article of manufacture includes an acetate film substrate and surface-selective converted polyhydroxy functional groups available for further reactive conversion or system fabrication of gas barrier layers in a multilayer film construction. Such a modification may offer either a single-sided or double-sided functional group conversion. The surface or surfaces may be further involved in polyol reactive processes, such as, for example, reaction with poly(glycerol sebacate) (PGS), poly(glycerol sebacate urethane) (PGSU), or poly(glycerol sebacate) acrylate (PGSA).

Various features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 4 schematically shows a process of forming a coated polymer film in an embodiment of the present disclosure.

FIG. 5 schematically shows a polymer film with a PGS surface in an embodiment of the present disclosure.

Wherever possible, the same reference numbers will be used throughout the drawings to represent the same parts.

DETAILED DESCRIPTION OF THE INVENTION

Figure 1:
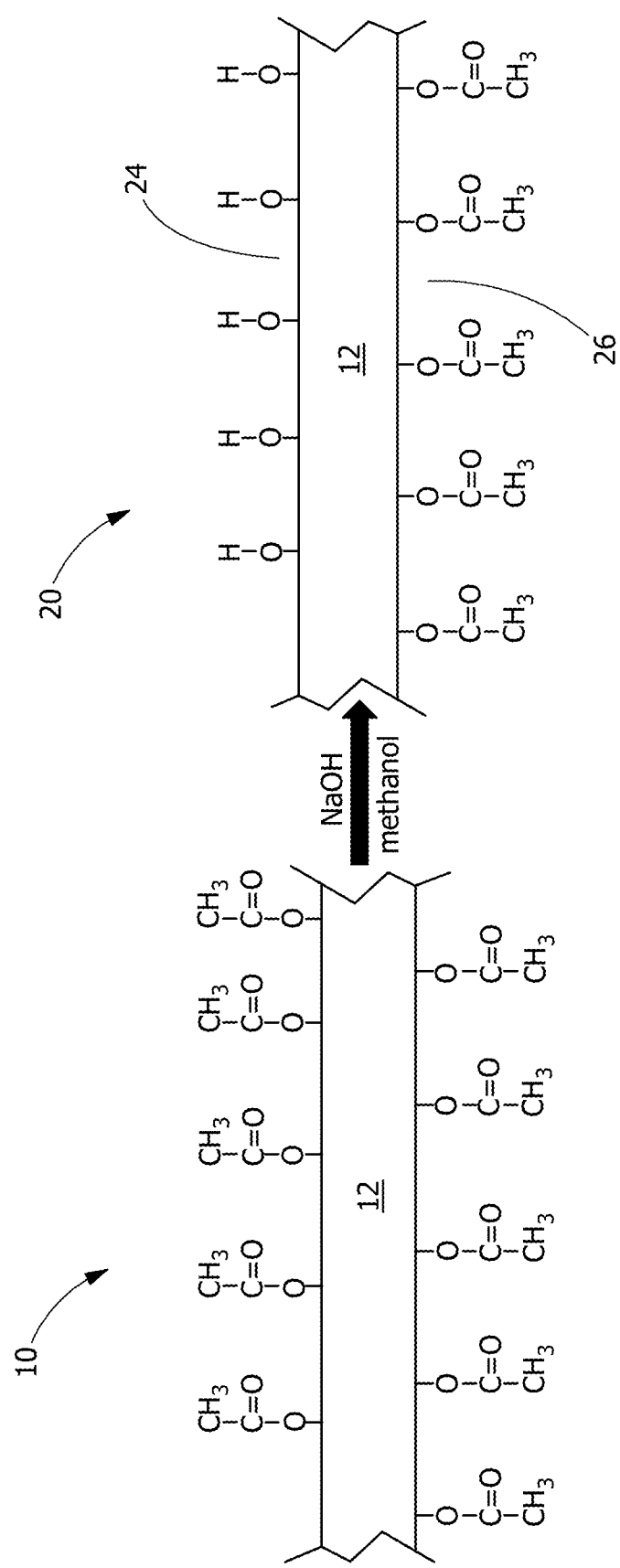
FIG. 1 schematically shows surface conversion of one surface of a PEVA film to PEVOH in an embodiment of the present disclosure.

A single film with variable functional group sides, such as PEVOH versus PEVA or PVOH versus PVA, permits like-sided surfaces to be annealed or apposed without the need for additional tie layers.

In exemplary embodiments, a composition of matter includes a PEVA substrate with a PEVOH-functionalized surface that is further modified. For example, PGS is a branched polyester with free carboxylic acid and alcohol functional groups (HO-PGS-COOH) capable of extending a polycondensation reaction through the carboxyl functional acid group with any available OH (hydroxy) group. Furthermore, PGS is composed of metabolite building blocks (glycerol and sebacic acid).

Conversion of the acetate surface functional groups of PEVA to a polyol-functionalized surface provides an opportunity to poly-condense PGS-COOH to the polyol-bearing film surface, thereby forming PEVOOC-PGS with an ester bond at the surface. Such an attachment to the surface allows the newly-converted surface to provide benefits resulting from the presence of PGS that may include, but are not limited to, surface erosion features, nutritional release of hydrolyzed or biodegraded building block metabolites into a SUB system or other biocontainment configuration, a controlled release film/surface for small active pharmaceutical ingredients (APIs) and biologics, a surface where cell attachment would be temporary as the result of eventual erosion, a new gas barrier technology, or a converted PEVA to PEVOH surface to additionally or further react with a poly isocyanate or other alcohol functional-reactive reagents to create a urethane surface. Such urethane surfaces may include, for example, a PGSU erodible surface, a polyurethane film coating to act as an exterior film-skin surface or protective coating, or a polyurethane gas barrier layer.

In some embodiments, the gas barrier layer is an oxygen barrier layer. In some embodiments, the oxygen barrier is beneficial for a blood or cryopreservation bag. In some embodiments, the oxygen barrier is useful for a bioreactor bag connected to a controller that meters gases into the bag, where very tight control over dissolved gas levels are needed to avoid the need to balance out for gas diffusion through the films. In some embodiments, a partial oxygen barrier is useful for simulating hypoxic conditions, such as, for example, for expanding T cells under hypoxic conditions as a method of selection to generate cells that are less impacted by a hypoxic solid tumor microenvironment.

Such a convertible surface provides a commercial option for a universal film, because the convertible surface may be further modified or customized for the reactor design.

In exemplary embodiments, the need for an expensive multilayer film is eliminated.

The acetate chemistry of PEVA is susceptible to hydrolysis under certain conditions, especially basic conditions. The hydrolysis of PEVA as an interior SUB film surface produces acetic acid, which is antagonistic to many biological metabolic conditions. The passivation of the surface with a plurality of active or inner surface modifications avoids this hydrolysis.

The avoidance of tie layers also avoids the potential contamination by extractables and leachables from formation of the tie layer.

In some embodiments, at least 10% of the acetate groups at a surface are converted to alcohol groups. In some embodiments, at least 25% of the acetate groups at a surface are converted to alcohol groups. In some embodiments, at least 50% of the acetate groups at a surface are converted to alcohol groups. In some embodiments, at least 75% of the acetate groups at a surface are converted to alcohol groups. In some embodiments, at least 90% of the acetate groups at a surface are converted to alcohol groups. In some embodiments, at least 95% of the acetate groups at a surface are converted to alcohol groups. In some embodiments, at least 99% of the acetate groups at a surface are converted to alcohol groups. In some embodiments, all or essentially all of the acetate groups at a surface are converted to alcohol groups.

In exemplary embodiments, the depth of surface conversion is controlled by the conditions under which the conversion occurs. Appropriate conversion depths may include, for example, at least 0.04 mil (1 μm), 0.04 mil (1 μm) to 0.4 mil (10 μm), 0.04 mil (1 μm) to 1 mil (25 μm), at least 0.2 mil (5 μm), 0.2 mil (5 μm) to 1 mil (25 μm), at least 0.4 mil (10 μm), 0.4 mil (10 μm) to 1 mil (25 μm), up to 1 mil (25 μm), or any value, range, or sub-range therebetween.

In exemplary embodiments, the level of conversion and the depth of conversion are selected to provide a strong surface bonding while still maintaining the bulk thermoplastic behavior of the PEVA or PVA polymer.

The modified surface allows for additional coupling agent chemistries, if desired. In exemplary embodiments, the process converts a non-bioactive surface into a potentially bio-active surface. The modified surface may allow for the incorporation of sidewall chemistries that support media control, such as, for example, acid scavenging or by-product elimination. The modified surface may allow for any alcohol-reactable chemistries to be affixed to side walls, including, but not limited to, certain polymers, biologics, biomolecules, and pharmaceutically active molecules, such as, for example, PGS. The modified surface also allows for hydrogen bonding to the surface of the film.

In an exemplary embodiment, a process converts the acetates of PVA to alcohols by a chemical saponification reaction, such as, for example, in a solvent, such as an alcohol, in the presence of a base. In some embodiments, the solvent is methanol and the base is sodium hydroxide, as shown schematically in Equation (1).

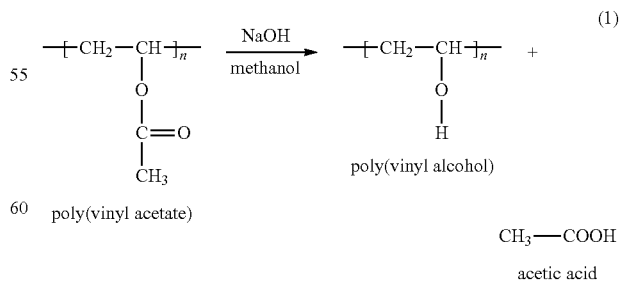

In other embodiments, the PVA surface may be oxidized with a plasma or other radiation chemical methods to convert the acetate groups to alcohol groups.

In another exemplary embodiment, a process converts the acetates of PEVA to alcohols by a similar chemical saponification reaction similar to the reaction (1) shown above for PVA. PEVA differs from PVA in having additional ethylene groups (—CH$_2$—CH$_2$—) along the polymer backbone. The materials and methods described herein are similarly applicable to PVA and PEVA polymer films.

In other embodiments, the PEVA surface may be oxidized with a plasma or other radiation chemical methods to convert the acetate groups to alcohol groups.

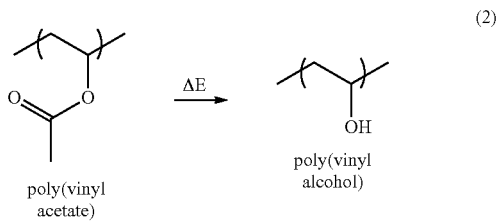

(2)

poly(vinyl acetate)        poly(vinyl alcohol)

For a film 10 of PEVA 12, the reaction occurs primarily at the exposed surface, as shown schematically in FIG. 1. Also shown in FIG. 1, when only one side 14 of the PEVA film 10 is exposed to the reagents, a modified film 20 of PEVOH results, where the modified film 20 has alcohol groups on one side 24 and acetate groups on the other side 26. The chemical makeup of the internal portion 12 of the modified film 20, however, is still substantially PEVA. The alcohol side 24 is then reactable by way of the alcohol groups at the surface of the alcohol side 24.

In exemplary embodiments, a process customizes the film surface for biological advantage or for chemical design and further film application. Considering the bioengineering control of SUB media and contents by process controllers, this approach allows customization of both the interior film surface and functionality to the bioprocess and the exterior film surface for manufacturing and handling.

In exemplary embodiments, a single film may be modified in a multitude of ways that preserve the two unique surface chemistries of the single film. The single film may be of any appropriate thickness with any appropriate hydroxy conversion depth. In an exemplary embodiment, the film is a 5-mil (130-µm) film with a conversion depth of up to 1 mil (25 µm). The conversion depth may be customized by modifying the details of the conversion process. The avoidance of a tie layer reduces extractables and leachables contamination. Thermoforming the SUB avoids contamination from sandwich oozing of middle layers with different chemical or physical properties.

In exemplary embodiments, customization of the SUB may affix selected materials as well as change the physical properties of the surface, such as, for example, its wettability, surface energy, and compatibility. In some embodiments, a convertible surface is modified to reduce or prevent cell adhesion to the surface. In some embodiments, a convertible surface is silanized to serve as a water repellant. In some embodiments, a convertible surface is modified to reduce adsorption of media components, such as proteins, peptides, antibiotics, interleukins, growth factors, nutrients, micronutrients, and/or adjuvants. In some embodiments, a convertible surface is modified to reduce adsorption of viral vectors during adeno-associated virus (AAV) or lentiviral (LV) manufacturing, thereby increasing the titer of the final gene therapy product. In some embodiments, a convertible surface is modified to prevent release of extractables and leachables from the underlying substrate, which may have negative effects on the contents of the SUB bag or may cause manufacturing issues in downstream processes.

As such, the surface of the SUB bag film becomes a potential part of the engineered-in design input, where the bag surface may be smart or active. As a smart surface, the polyol surface may also allow for spontaneous self-assembly or accumulation of an active biologic as part of a harvesting, purification, or sequential culturing method. In exemplary embodiments, this permits the modified, convertible film to serve as a universal film for almost any SUB bag application.

Figure 2:
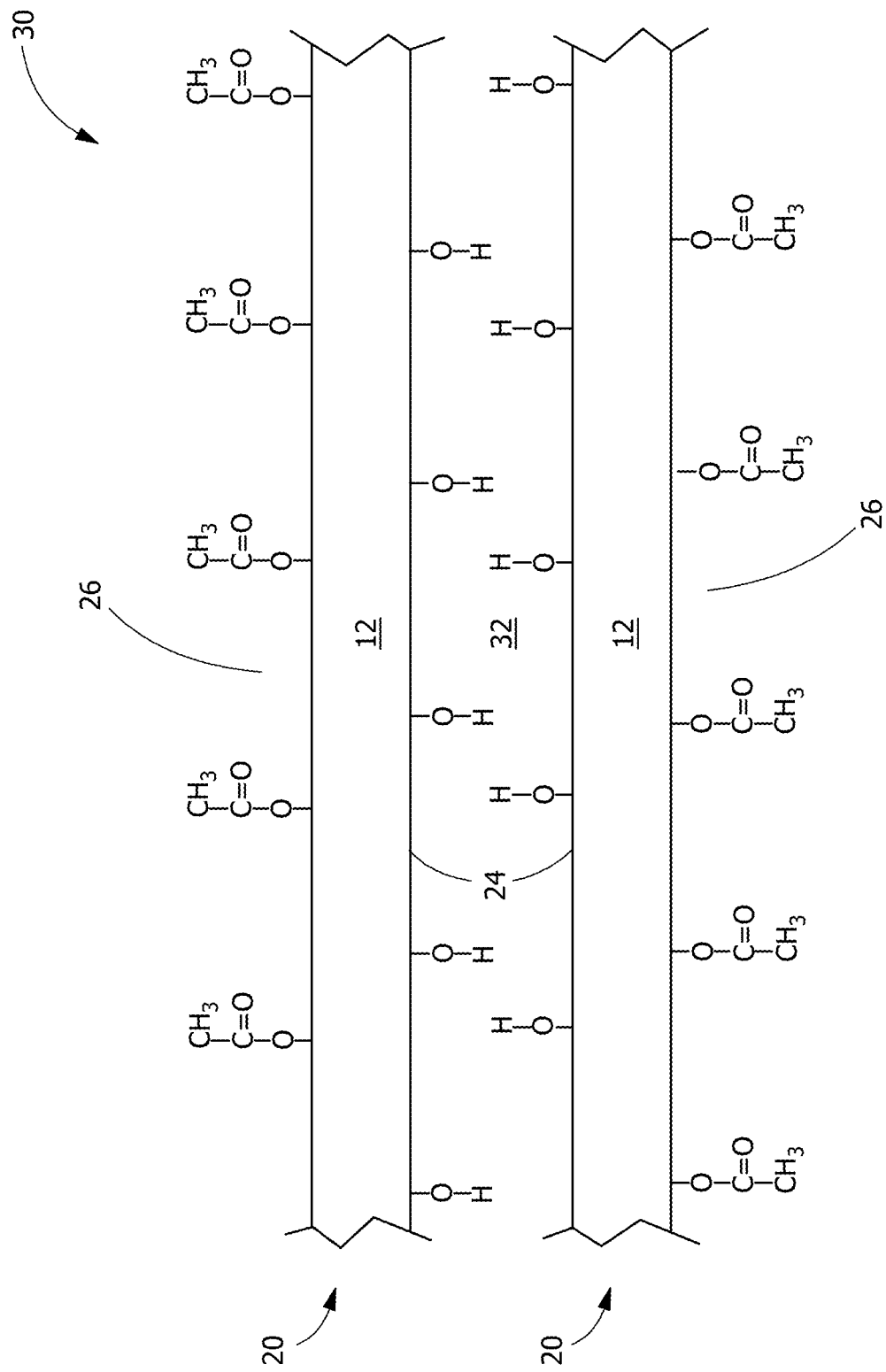
FIG. 2 schematically shows a polymer film formed by annealing two polymer films of FIG. 2 together in an embodiment of the present disclosure.

In exemplary embodiments, modified surfaces of two modified films 20 may be annealed together to create a film 30 with two PEVA surfaces 26, two internal portion 12 of substantially PEVA, and an internal PEVOH barrier layer 32 without the presence of a tie layer, as shown schematically in FIG. 2. In some embodiments, the film 30 is formed by laying the alcohol sides 24 of two modified films 20 to face each other and heat annealing them together.

Figure 3:
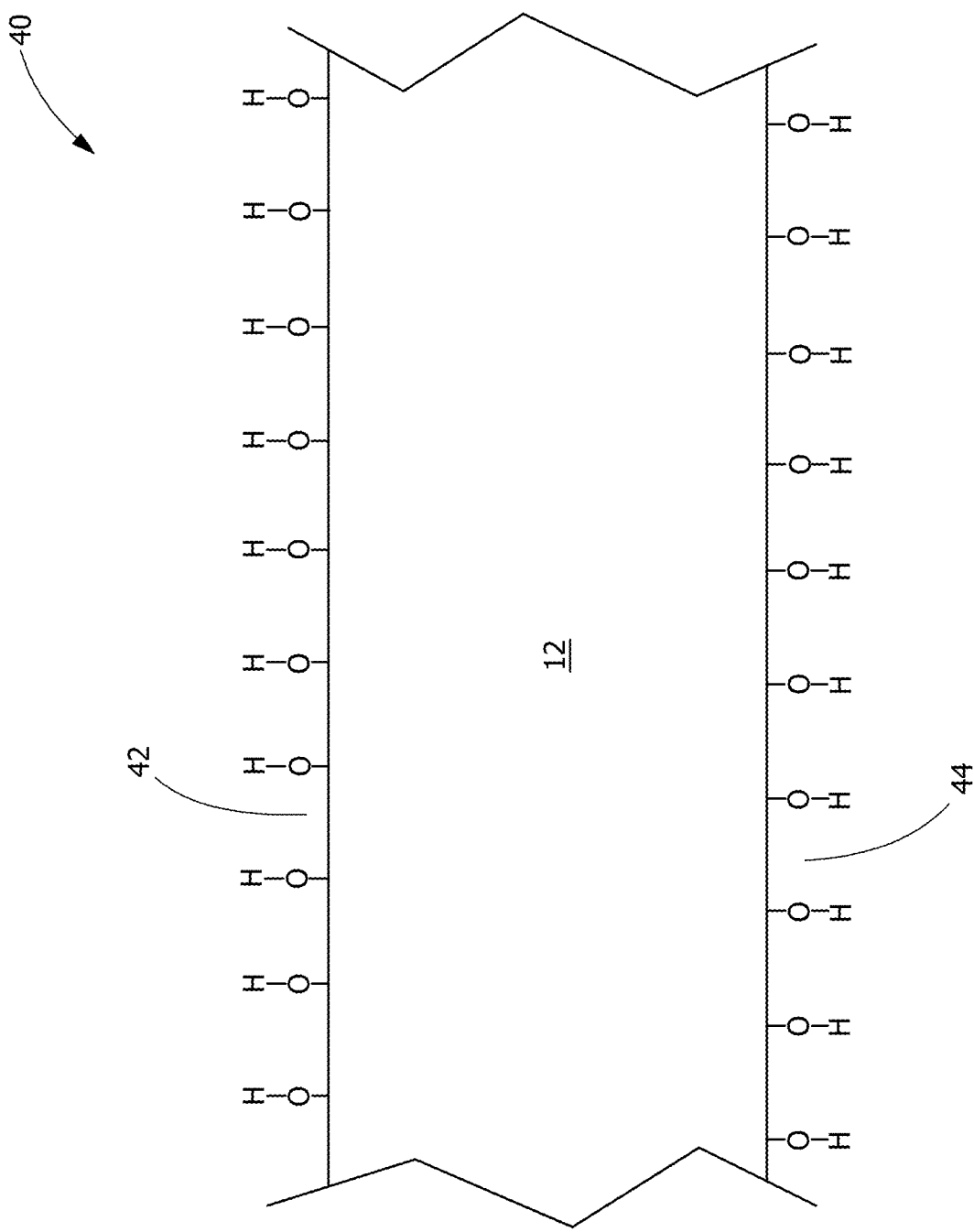
FIG. 3 schematically shows a polymer film with different conversions on the two surfaces in an embodiment of the present disclosure.

In other exemplary embodiments, both surfaces of a PEVA film 10 are converted to alcohol groups, to form a modified film 40 with an internal portion 12 of substantially PEVA, a first surface 42 of PEVOH and a second surface 44 of PEVOH, as shown schematically in FIG. 3. In some embodiments, the modified film 40 forms a biocontainment bag with the first surface 42 being the interior bag surface and being functionalized differently from the second surface 44 as the exterior bag surface. In some embodiments, the first surface 42 is converted to a biologic-based surface. In some embodiments, the second surface 44 is converted to a protective treatment, such as, for example, a urethane or an ester.

In some embodiments, the first surface 42 is converted to a biologic-based surface, since it will be exposed to the bioreactor contents. The second surface 44 may be converted to a protective surface, such as, for example, a urethane or an ester.

In exemplary embodiments, formation of a PEVOH film with a coating layer follows the continuous web process 50 shown schematically in FIG. 4. The coating layer includes an alcohol-reactable coating composition. In exemplary embodiments, the alcohol-reactable coating composition is a polymer. In some embodiments, the alcohol-reactable coating composition includes PGS and the surface coating is a PGS-functionalized coating.

The PEVA film 52 coming off a spool 54 is fed through a festoon setup 56 of alternating baths of sodium hydroxide 58 and water rinses 60 to convert surface acetate groups to alcohol groups. A coating layer 62 is then applied to at least one surface, followed by curing 64, which causes the alcohol-reactable coating composition to covalently attach to the hydroxy surface, thereby forming the coated PEVOH film 66.

In some embodiments, the curing 64 is by microwave energy. The other surface of the PEVA film may be left unmodified or may be modified in the same or a different manner.

As shown schematically in FIG. 5, the coated PEVOH film 66 includes the internal portion 12 of substantially PEVA with an acetate surface 26 and the alcohol side 24 attached to the coating layer 62. In some embodiments, the process includes applying the coating layer 62 by spraying the coating composition onto the side 24 of the modified film 20 having alcohol groups. In some embodiments, the coating layer 62 is applied by dip coating the coating composition onto the side 24 of the modified film 20 having alcohol groups. In some embodiments, the coating composition includes a copolymer of glycerol and sebacic acid. In some embodiments, the copolymer of glycerol and sebacic acid further includes citric acid. In some embodiments, the copolymer of glycerol and sebacic acid further includes citric acid as a constituent monomer and is, therefore, a copolymer of glycerol, sebacic acid, and citric acid. In some embodiments, the presence of the citric acid reduces the cure time and/or the cure temperature for the curing of the coating layer 62. In some embodiments, the surface coating 62 is an inner surface of a single-use bioreactor bag, and the citric acid, such as, for example, upon release by degradation of the copolymer, provides buffering to modulate the pH of the contents of the single-use bioreactor bag.

In exemplary embodiments, the citric acid-containing copolymer of PGS acts as an anticoagulant and, with the addition of adenine, provides a SUB blood storage system.

Figure 6:
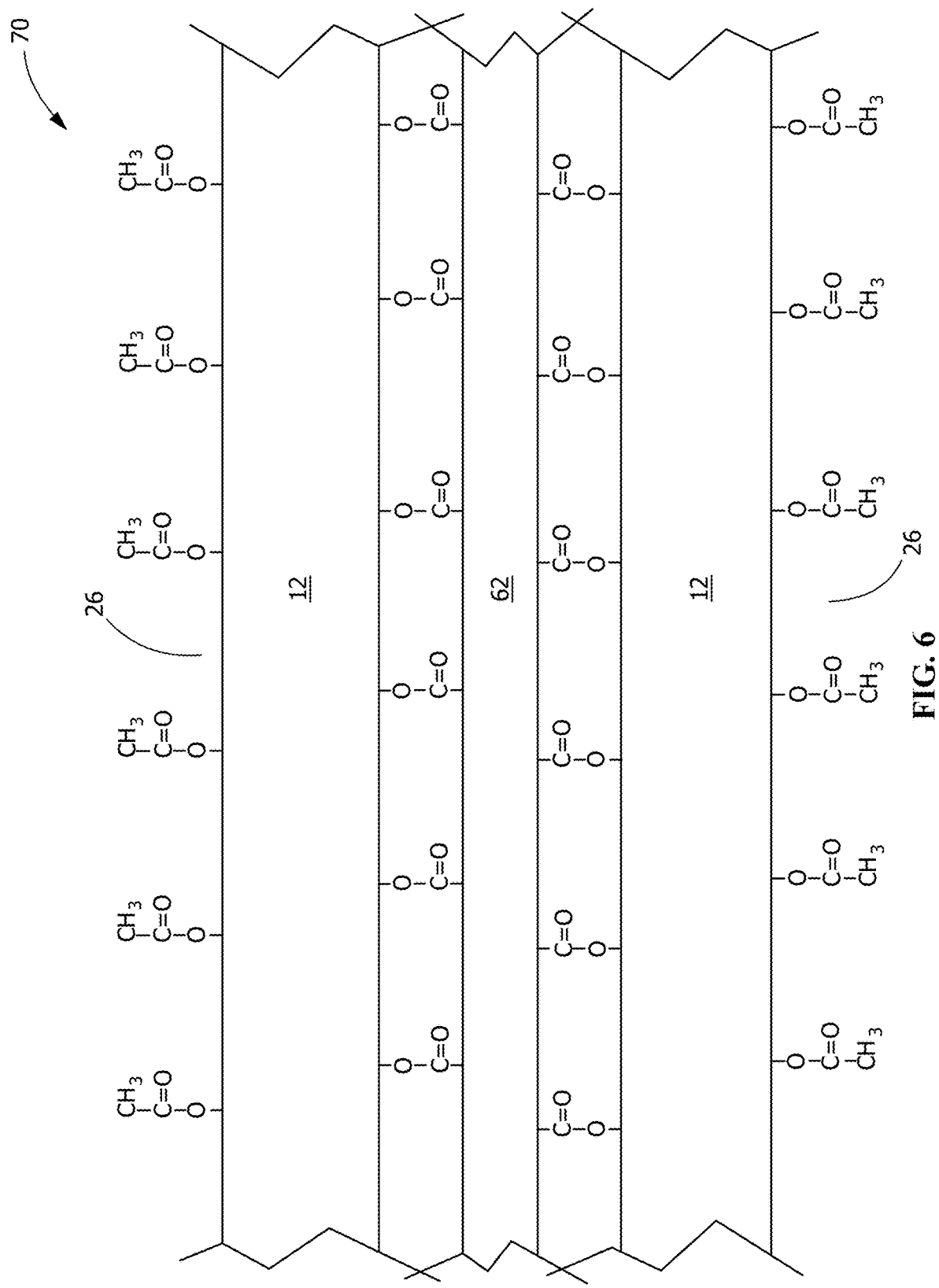
FIG. 6 schematically shows a polymer film with a PGS barrier layer in an embodiment of the present disclosure.

FIG. 6 shows two PEVA films with PGS barrier coatings 66 fused together by their PGS coatings 62 to form a film 70 with two acetate surfaces 26, two internal portions 12 of substantially PEVA, and the PGS coatings 62 becoming an internal PGS layer 62.

In another embodiment, a process includes photo conversion of acetate groups to alcohol groups by selective photo-oxidation with radiation, such as, for example, gamma radiation, X-ray radiation, ultraviolet (UV) radiation, or infrared (IR) radiation.

In another embodiment, a process includes a plasma film etch to convert acetate groups to alcohol groups, such as to convert PVA to PVOH.

Following the conversion step, the converted film may be rinsed and dried to remove any residual conversion by-products and the surface treatment may be equilibrated prior to analysis.

In other embodiments, the above plasma film etch process instead converts acetate groups of PEVA to alcohol groups, thereby converting PEVA to PEVOH at the surface to provide alcohol (hydroxy) groups at the surface.

In exemplary embodiments, the surface conversion may be analyzed by one or more non-destructive methods, which may include, but are not limited to, Fourier-transform infrared (FT-IR) spectroscopy, variable angle infrared (IR) spectroscopy, Raman spectroscopy, scanning electron microscopy (SEM), conductivity measurements, or contact angle measurements.

Such analysis may establish the type and degree of functional group conversion, the depth of the surface conversion, and/or the conversion stability. For example, variable angle IR spectroscopy may be used to determine the depth of conversion to hydroxy groups.

A single film with a dual reactive side characteristic opens up numerous possibilities to develop coatable and reactable film surfaces for low-temperature applications.

Figure 7:
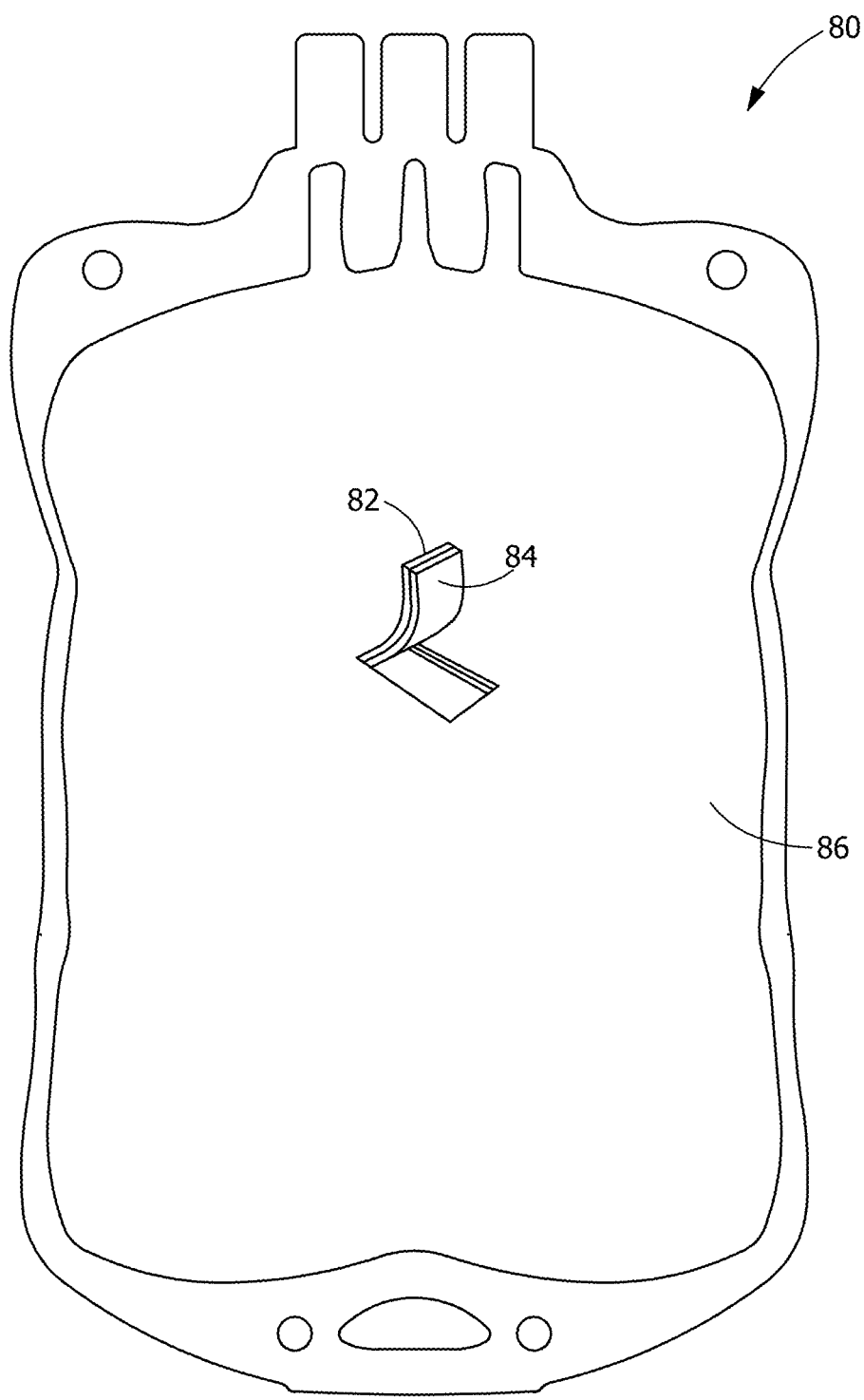
FIG. 7 schematically shows a biocontainment bag in an embodiment of the present disclosure.

FIG. 7 shows a partial perspective view of a biocontainment bag 80. The biocontainment bag 80 includes a vessel structure defining an enclosed or contained space. The biocontainment bag 80 is formed of a film 82 having an inner surface 84 and an outer surface 86. Although the film 82 is shown as having two layers in FIG. 7, the film 82 may be any number of layers and may have any of the structures and may include any of the coatings or surface modifications described herein.

In addition to PGS functionalization, other functionalizations of the film surface through the alcohol group may include, but are not limited to, PGSU, PGSA, free isocyanate, a polyurea polymer, an isocyanate-functional polyurethane, carboxyl functional materials, short chain fatty acids, biologics with carboxyl functionality, or any other structure capable of reacting or associating with a hydroxy group.

The process may be applicable to a multitude of surfaces where cell and gene biology is required to have biocompatible or bioactive status. PEVOH surfaces are excellent bonding surfaces and therefore are potentially good surface treatments for adhesive methodologies including bioreactor fabrication. Creating a surface of PGS bound to PEVOH may also provide a two-dimensional culture surface where the wet reactor conditions are not conducive for cell expansion. The process may alternatively convert acetate fibers for biofiltration or bioreactor use. The process may alternatively provide only a mild surface conversion that modifies the wettability of the surface. The oxygen on a convertible surface may behave as a nucleophile and consequently promote reactivity.

The process may include the benefit of PEVA low temperature service with surface modification rather than having to depend on film lamination.

In some embodiments, a polymerization initiator may be attached to the alcohol group, or the alcohol group itself may be used as a polymerization initiator, for a polymerization at the surface of the film. As such, different polymers may be placed on the film surface, allowing for tunable film and surface properties.

In some embodiments, certain sections of the PEVA film surface may be masked or otherwise blocked during saponification to provide spatial control on the film for where the conversion is occurring. The appending of the functional groups to certain sections of the film surface may then be done while keeping it away from other sections.

In some embodiments, the structure being appended to attach to the alcohol group may be activated to aid in connecting to the surface hydroxy groups. For example, PGS may be activated to convert the carboxylic acid groups to an activated ester, such as, for example, with N-hydroxysuccinimide (NHS); a carbodiimide, such as, for example, N,N'-dicyclohexylcarbodiimide (DCC), 1-ethyl-3-(3-dimethylaminopropyl)carbodiimide (EDC), or N,N'-diisopropylcarbodiimide (DIC); or an acid chloride.

In some embodiments, the modified film may be used for chelating metal catalysis for various applications. For example, a tube may be lined with or made of PEVA, with the surface acetates being converted to hydroxy groups that have the ability to chelate metals. The chelated metals may then be used for catalysis. Alternatively, the hydroxy groups may be used for extracting metal out of water.

Although described herein primarily for SUB construction, the processes and films may also be applicable to solid state reactor designs, filtration, and accessory utilization to cell-based and bioprocessing systems.

Additionally, these processes may be extendable to PEVA articles of manufacture or material moieties other than films, such as, for example, fibers. For example, the surfaces of PEVA fibers may be converted to PEVOH surfaces as a pretreatment or surface-functional platform for textile treatment, for drug delivery, or as a sheath-core coating.

EXAMPLES

The invention is further described in the context of the following examples which are presented by way of illustration, not of limitation.

Example 1

A 2-cm by 2-cm PEVA film was placed in a scintillation vial with 10 mL of a 1.5 M solution of sodium hydroxide in methanol. The vial was maintained on a hotplate for 48 hours at a set temperature of 50° C. (122° F.). The test film was then removed from the vial, washed with deionized (DI) water, and patted dry. A control film of PEVA was washed with DI water and patted dry. The test film and the control film were each individually evaluated by attenuated total reflectance (ATR) FT-IR spectroscopy, with the resulting spectra being shown in FIG. 8.

Figure 8:
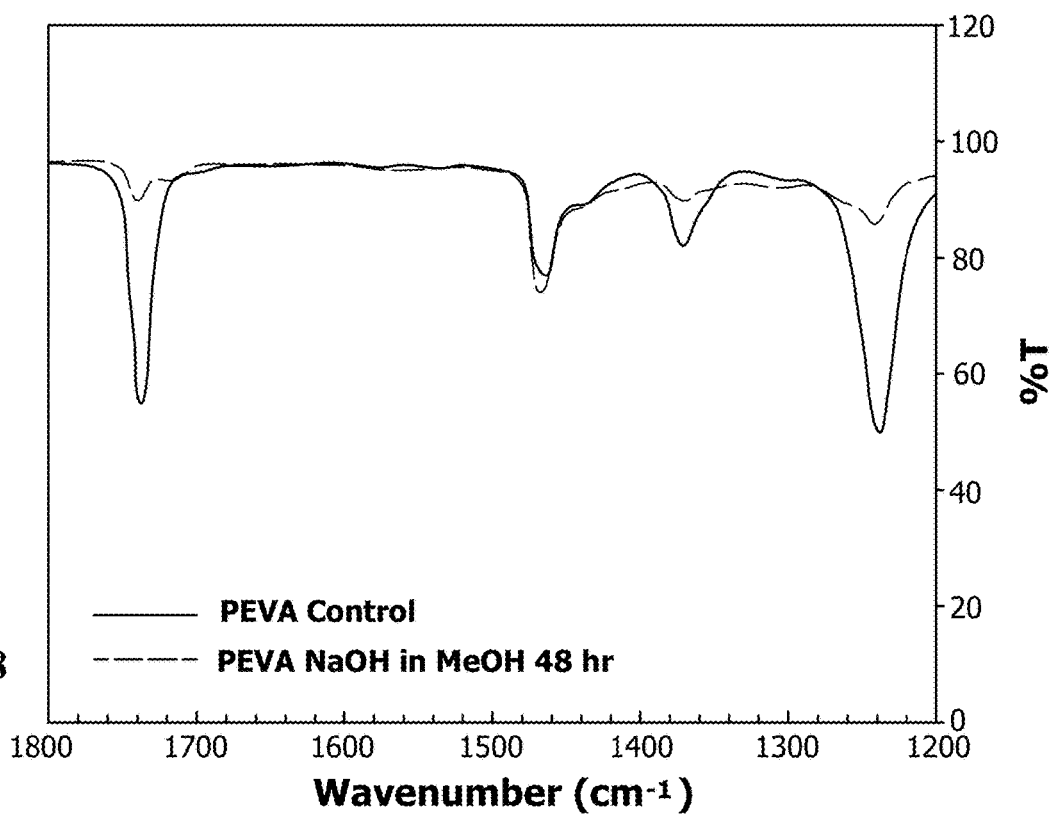
FIG. 8 shows Fourier-transform infrared (FT-IR) spectra of a PEVA control film and a converted PEVA film.

The FT-IR spectra in FIG. 8 show a decrease of intensity at a wavenumber of about 1740 cm$^{-1}$ and an increase of a broad peak at a wavenumber of about 3300 cm$^{-1}$ for the test film relative to the control film, indicating a decrease in ester functionality and an increase in hydroxy functionality in the test film relative to the control film, consistent with the surface acetate groups of the PEVA having been converted to hydroxy groups in the test film.

More specifically, the control PEVA film structure can be described as an aliphatic vinyl backbone with an acetate pendent group. Furthermore the acetate group includes of an ester carbonyl and a methyl group (—CH$_3$).

The PEVA control ester carbonyl is identified at about 1740 cm$^{-1}$. The acetate methyl group (wag) is present at about 1350 cm$^{-1}$ in the control spectrum. Note in FIG. 8 that both the acetate 1740 cm$^{-1}$ carbonyl groups and 1350 cm$^{-1}$ methyl groups are lost in the treated sample with the formation of a new —OH band at 3300 cm$^{-1}$ (not shown in FIG. 8) as a result of the process, indicating an efficient loss of acetate pendent groups and conversion of the surface acetate pendent groups to available reactable hydroxy groups. Additionally, the ATR depth of penetration is about 13 µm (0.5 mil), indicating a surface conversion of substantial depth for alcohol-reactable bonding. In other words, the conversion process provides the appropriate surface chemistry for both PGS and PGSU since the film bonding involves both or either polycondensation or isocyanate reactivity.

Thus, this surface conversion has created an indigenous-functional polymer-bound coupling surface, as shown schematically in FIG. 1. This is in contrast to using a coupling agent surface treatment. This is a benefit over coupling agents, because coupling agent surface treatments are notorious for having blind or unreacted regions or spots.

Example 2

Figure 9:
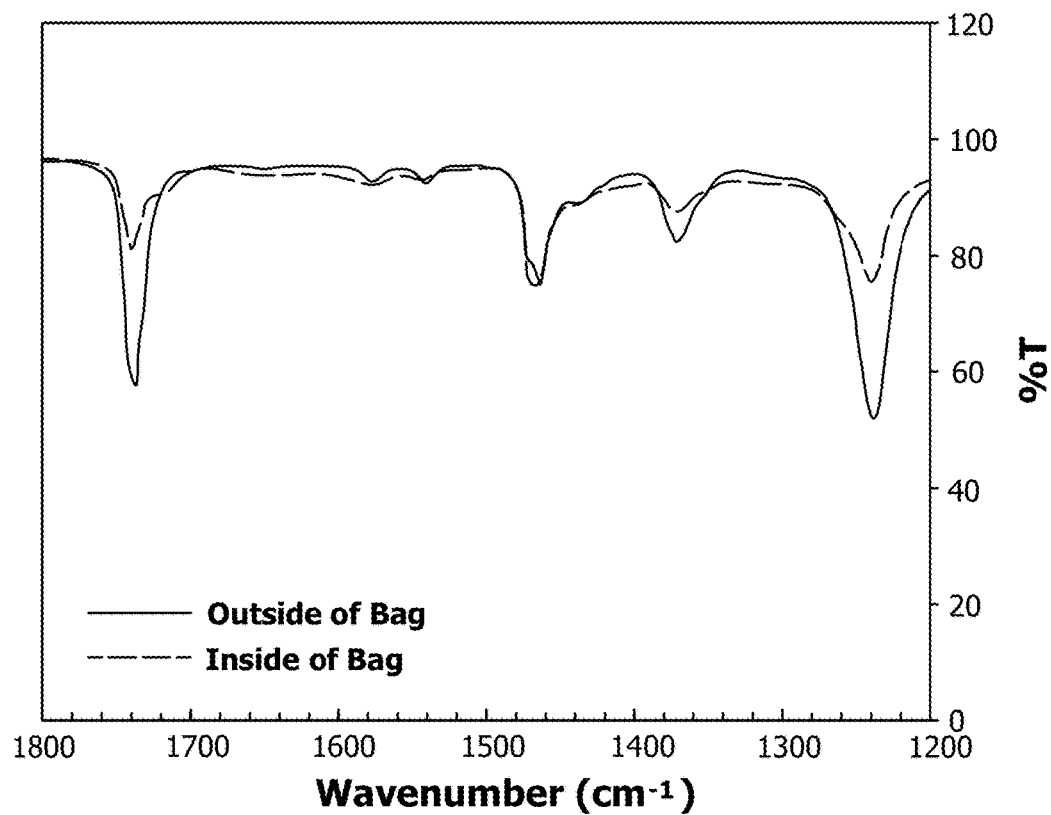
FIG. 9 shows FT-IR spectra of the outside surface and the inside surface of a biocontainment bag.

The interior surface but not the exterior surface of a bag was exposed to saponification conditions similar to those described for Example 1. Referring to FIG. 9, ATR FT-IR spectroscopy of the interior surface and the exterior surface show greater hydroxy functionality on the interior surface than the exterior surface, indicating conversion of the acetate group in PEVA to an alcohol functionality on the interior surface.

Example 3

Figure 10:
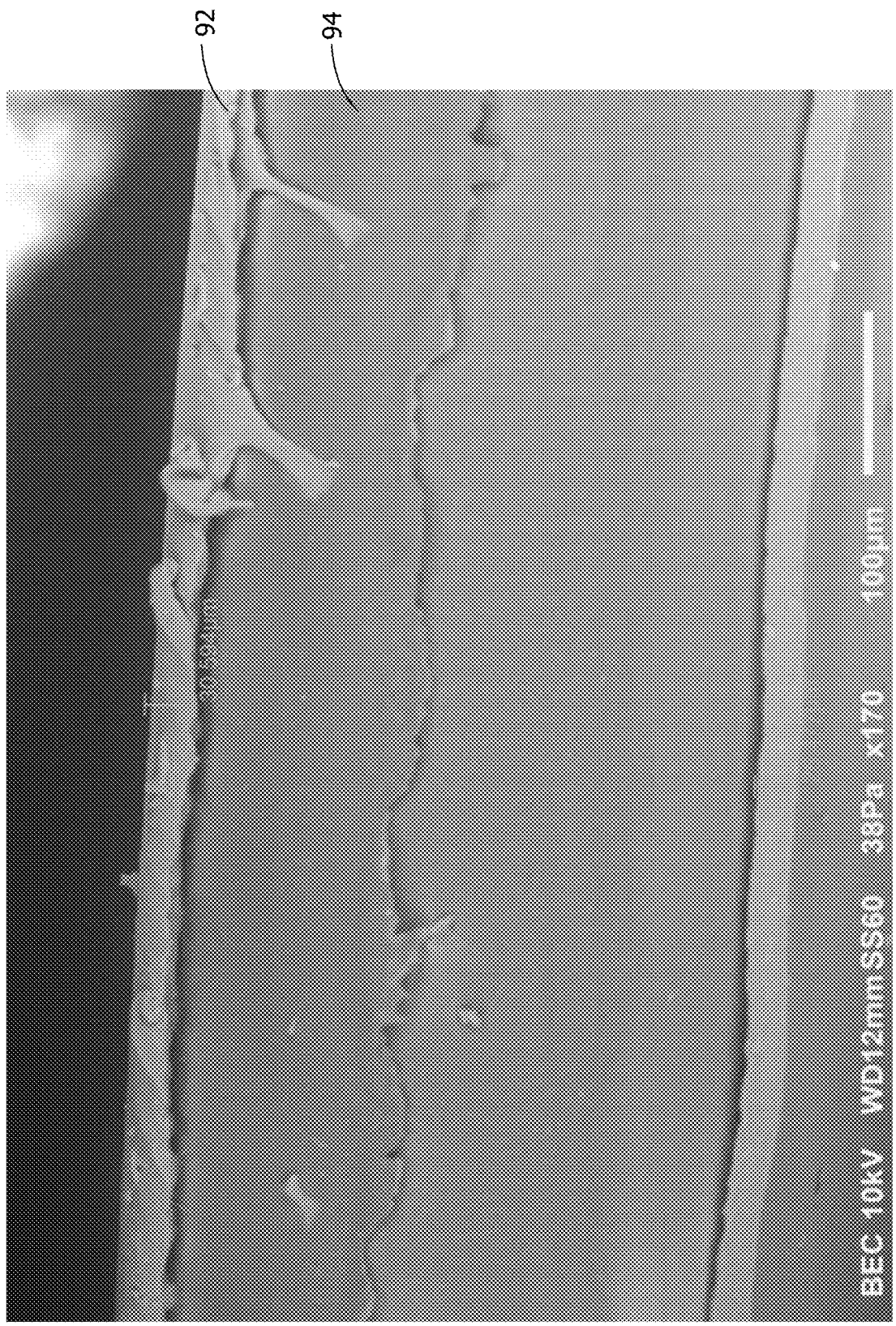
FIG. 10 shows a PGS coating on a PEVOH surface of a PEVA film.

A converted PEVA film was prepared as described for Example 1. A 40% solution of PGS was made in THF with tin octanoate (2% w/w with respect to PGS) added as a catalyst. The converted PEVA film was submersed in the PGS solution for 30 seconds, removed and cured in a 90° C. oven for 3 days at a pressure 10 torr, resulting in deposition of a PGS coating 92 having a thickness of about 30 µm on the converted PEVA film 94, as shown in FIG. 10.

Example 4

A PGS-citric acid co-polymer was formed by first charging sebacic acid (200 g, 0.989 mol), glycerol (80.2 g, 0.89 mol), citric acid (19 g, 0.09 mol), and water (23 g, 1.28 mol) to a reactor. The mixture was then heated to melt under a blanket of nitrogen. Once the mixture melted, the reactor was set to a temperature of 120° C. for 24 hours. The reaction was then put under vacuum at 10 torr at 130° C. for 26 hours. The polymer was then cooled to a white solid. Gas permeability chromatography indicated a Mw of about 4300 and a Mw/Mn of about 3.9.

Example 5

A converted PEVA film was prepared as described for Example 1. A solution was made of 15% PGS-citric acid co-polymer of Example 4 in THF with tin octanoate (1% w/w) as a catalyst. The PGS co-polymer solution was spray coated onto the converted PEVA film and cured at 85° C. under a N$_2$ atmosphere for 24 hours.

Example 6

The sample of Example 5 was evaluated for oxygen, carbon dioxide, and water vapor transmission rates following ASTM F-622, ASTM F-2476, and ASTM-1249 methods, respectively. The oxygen, carbon dioxide, and water vapor transmission rates for the converted PEVA film were 1975 cc/m$^2$/day, 6870 cc/m$^2$/day, and 10.7 g/m$^2$/day, respectively. These values decreased to 610 cc/m$^2$/day, 3145 cc/m$^2$/day, and 5.31 g/m$^2$/day, respectively, after coating and curing of the PGS-citric acid film, demonstrating that the PGS film acts as an efficient gas barrier film.

All above-mentioned references are hereby incorporated by reference herein.

While the invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A polymer film comprising:
   a base layer of a first composition of poly(ethylene-vinyl acetate);
   a surface layer at a surface of the base layer, the surface layer comprising surface hydroxy groups converted from acetate groups of the poly(ethylene-vinyl acetate); and
   a coating layer of a second composition of a copolymer of glycerol, sebacic acid, and citric acid;
   wherein the second composition is attached to the surface layer by ester bonds between carboxyl groups of the copolymer of glycerol, sebacic acid, and citric acid and the hydroxy groups of the surface layer.

2. The polymer film of claim 1, wherein the copolymer of glycerol, sebacic acid, and citric acid is a urethane.

3. The polymer film of claim 1, wherein the copolymer of glycerol, sebacic acid, and citric acid is an acrylate.

4. The polymer film of claim 1, wherein the surface layer is on a single side of the base layer.

5. The polymer film of claim 1, wherein the surface layer is on a first side of the base layer and a second side of the base layer opposite the first side.

6. The polymer film of claim 1, wherein the hydroxy groups of the surface layer extend a conversion depth of up to about 1 mil.

7. A single-use bioreactor bag comprising a polymer film comprising:
   a base layer of a first composition of poly(ethylene-vinyl acetate);
   a surface layer at a surface of the base layer, the surface layer comprising surface hydroxy groups converted from acetate groups of the poly(ethylene-vinyl acetate); and
   a coating layer of a second composition of a copolymer of glycerol, sebacic acid, and citric acid;
   wherein the second composition is attached to the surface layer by ester bonds between carboxyl groups of the copolymer of glycerol, sebacic acid, and citric acid and the hydroxy groups of the surface layer.

8. The single-use bioreactor bag of claim 7, wherein the surface layer is on a single side of the polymer film.

9. The single-use bioreactor bag of claim 7, wherein the surface layer is on a first side of the polymer film and a second side of the polymer film opposite the first side.

10. The single-use bioreactor bag of claim 7, wherein the surface layer extends a conversion depth of up to about 1 mil.

11. The single-use bioreactor bag of claim 7, wherein the coating layer is an inner surface of the single-use bioreactor bag, and the citric acid provides buffering to modulate a pH of a content of the single-use bioreactor bag.

12. A method of modifying a poly(ethylene-vinyl acetate) film, the method comprising:
   converting acetate groups at a first surface of the poly(ethylene-vinyl acetate) film to hydroxy groups; and
   applying a coating at the first surface, the coating comprising a copolymer of glycerol, sebacic acid, and citric acid;
   wherein the coating is attached at the first surface by ester bonds between carboxyl groups of the copolymer of glycerol, sebacic acid, and citric acid and the hydroxy groups.

13. The method of claim 12, wherein the converting comprises a process selected from the group consisting of saponification, radiation oxidation, plasma treatment, laser ablation, and laser oxidation.

14. The method of claim 12, wherein the converting converts acetate groups to hydroxy groups to a conversion depth of up to about 1 mil into the poly(ethylene-vinyl acetate) film.

15. The method of claim 12, wherein the converting also converts acetate groups at a second surface of the poly(ethylene-vinyl acetate) film opposite the first surface to hydroxy groups.

16. The method of claim 12, wherein the applying comprises spraying the coating on the first surface.

17. The method of claim 12, wherein the applying comprises dip coating the coating on the first surface.

18. The method of claim 12 further comprising curing the coating to the first surface to covalently attach the coating to the first surface.

19. The method of claim 18, wherein the citric acid reduces a time and a temperature for the curing.

\* \* \* \* \*